(12) United States Patent
Minola

(10) Patent No.: US 9,694,334 B2
(45) Date of Patent: Jul. 4, 2017

(54) GAS DIFFUSION SYSTEM AND METHOD FOR INTRODUCING A GAS STREAM IN AN APPARATUS, IN PARTICULAR A PASSIVATING GAS STREAM IN A UREA PLANT

(71) Applicant: SAIPEM S.p.A., San Donato Milanese (IT)

(72) Inventor: Paolo Minola, Peschiera Borromeo (IT)

(73) Assignee: SAIPEM S.P.A., San Donato Milanese (IT)

( * ) Notice: Subject to any disclaimer, the term of this patent is extended or adjusted under 35 U.S.C. 154(b) by 0 days.

(21) Appl. No.: 14/902,814

(22) PCT Filed: Jul. 4, 2014

(86) PCT No.: PCT/IB2014/062877
§ 371 (c)(1),
(2) Date: Jan. 4, 2016

(87) PCT Pub. No.: WO2015/001536
PCT Pub. Date: Jan. 8, 2015

(65) Prior Publication Data
US 2016/0175795 A1    Jun. 23, 2016

(30) Foreign Application Priority Data

Jul. 5, 2013    (IT) .............................. MI2013A01139

(51) Int. Cl.
*B01F 3/00* (2006.01)
*B01F 3/04* (2006.01)
(Continued)

(52) U.S. Cl.
CPC ........... *B01J 4/002* (2013.01); *B01F 3/04248* (2013.01); *B01F 3/04262* (2013.01);
(Continued)

(58) Field of Classification Search
CPC .......... B01F 3/00; B01F 3/04; B01F 3/04099; B01F 3/04106; B01F 3/04113;
(Continued)

(56) References Cited

U.S. PATENT DOCUMENTS 3,608,834 A    9/1971  MacLaren
4,460,130 A    7/1984  Baumann et al.
(Continued)

FOREIGN PATENT DOCUMENTS

DE    10 2010 053 289 A1    6/2012
WO    WO 2007/014085 A1    2/2007

OTHER PUBLICATIONS

Notification Concerning Submission, Obtention or Transmittal of Priority document for International Application No. PCT/IB2014/062877 dated Oct. 2, 2014.
International Search Report and Written Opinion for International Application No. PCT/IB2014/062877 dated Mar. 18, 2015.
PCT Demand for International Preliminary Examination and Reply to International Search Report and the associated Written Opinion for International Application No. PCT/IB2014/062877 dated Jun. 10, 2015.
(Continued)

*Primary Examiner* — Natasha Young
(74) *Attorney, Agent, or Firm* — Neal, Gerber & Eisenberg LLP

(57) ABSTRACT

A gas diffusion system configured to feed a gas stream, in particular a passivating gas stream, into an apparatus, in particular a decomposer, of a urea plant; the system extends along an axis and has a gas feed conduit having an outlet from which the gas flows substantially parallel to the axis, and a diffuser assembly configured to diffuse the gas supply from the conduit; the diffuser assembly is shaped so as to intercept the gas stream flowing axially from the outlet, and divert the gas stream substantially radially with respect to the axis and uniformly about the axis.

32 Claims, 7 Drawing Sheets

(51) Int. Cl.
  *B01J 4/00* (2006.01)
  *B01J 10/00* (2006.01)
  *B01J 19/00* (2006.01)
  *B01J 19/24* (2006.01)
  *C07C 273/00* (2006.01)
  *C07C 273/02* (2006.01)
  *C07C 273/04* (2006.01)

(52) U.S. Cl.
  CPC .............. *B01J 10/002* (2013.01); *B01J 19/24* (2013.01); *C07C 273/02* (2013.01); *C07C 273/04* (2013.01); *B01F 2003/0429* (2013.01); *B01F 2003/04304* (2013.01); *B01F 2003/04319* (2013.01); *B01F 2003/04368* (2013.01); *B01J 2219/1946* (2013.01); *B01J 2219/24* (2013.01); *Y02P 20/142* (2015.11)

(58) Field of Classification Search
  CPC .............. B01F 3/04241; B01F 3/04248; B01F 3/0462; B01J 4/00–4/002; B01J 10/00; B01J 10/002; B01J 19/00; B01J 19/24; B01J 2219/19; B01J 2219/194; B01J 2219/1941; B01J 2219/1946; B01J 2219/24; Y02P 20/00; Y02P 20/10; Y02P 20/14–20/142; C07C 273/00; C07C 273/02; C07C 273/04
  See application file for complete search history.

(56) References Cited

U.S. PATENT DOCUMENTS

| | | | |
|---|---|---|---|
| 4,859,430 A | * | 8/1989 | Julian .................... C10G 11/18 239/557 |
| 5,407,647 A | | 4/1995 | Tarancon |
| 2001/0031893 A1 | | 10/2001 | Pagani et al. |
| 2002/0054840 A1 | | 5/2002 | Lagana |
| 2011/0213186 A1 | | 9/2011 | Di Girolamo et al. |
| 2012/0068111 A1 | | 3/2012 | Shaikh |
| 2012/0193818 A1 | | 8/2012 | Hirose et al. |

OTHER PUBLICATIONS

Notification of Receipt of Demand by Competent International Preliminary Examining Authority for International Application No. PCT/IB2014/062877 dated Jun. 24, 2015.

Notification Concerning Informal Communications with the Applicant for International Application No. PCT/IB2014/062877 dated Jul. 20, 2015.

Reply to the Written Opinion of the International Searching Authority for International Application No. PCT/IB2014/062877 dated Aug. 3, 2015.

Notification of Transmittal of the International Preliminary Report on Patentability for International Application No. PCT/IB2014/062877 dated Oct. 29, 2015.

* cited by examiner

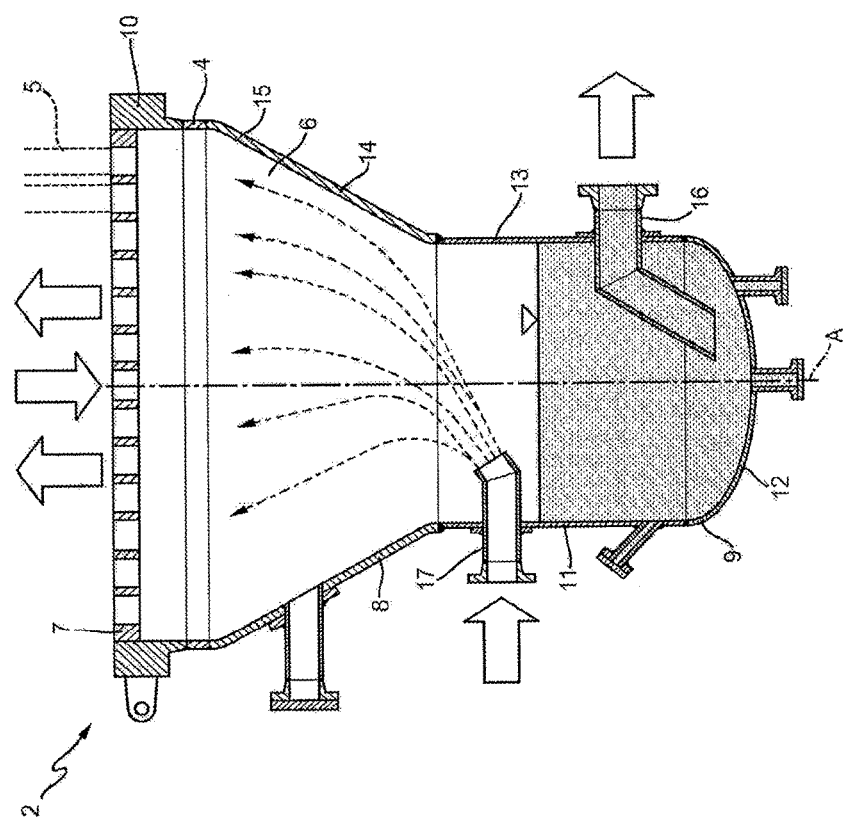

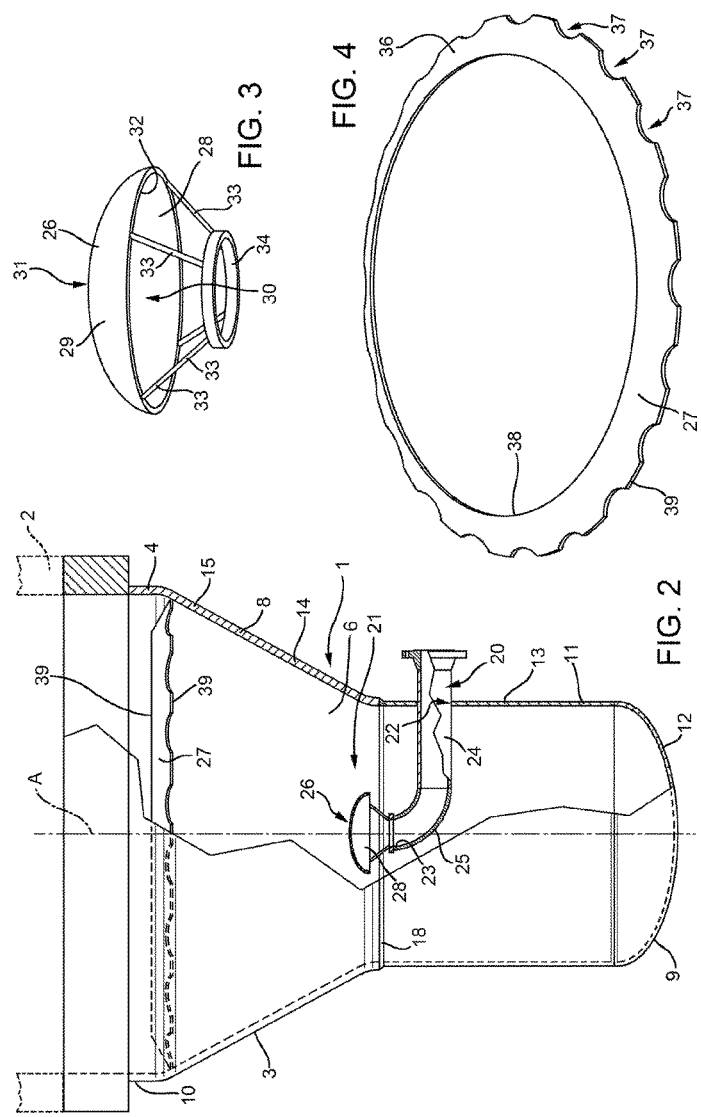

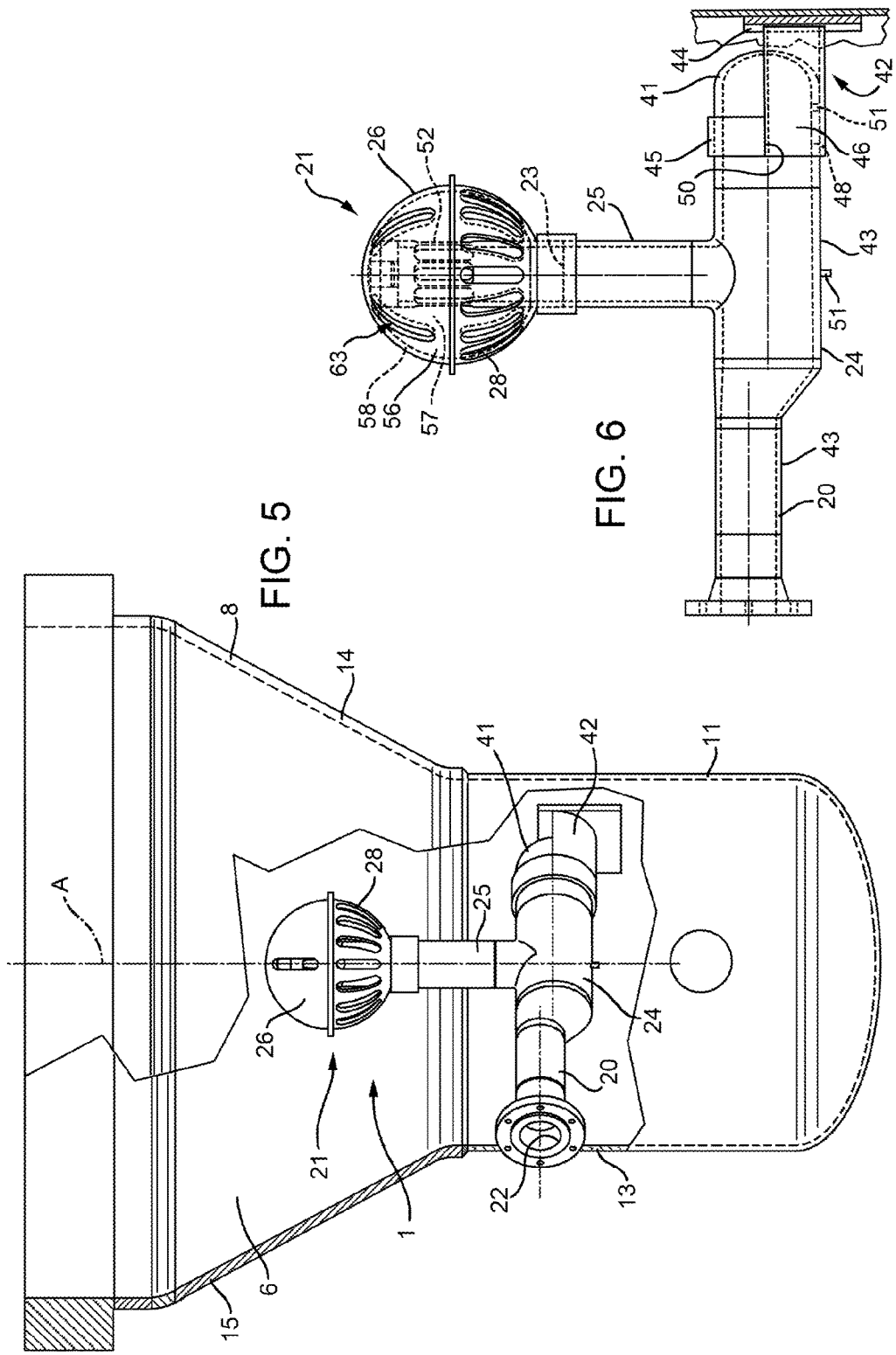

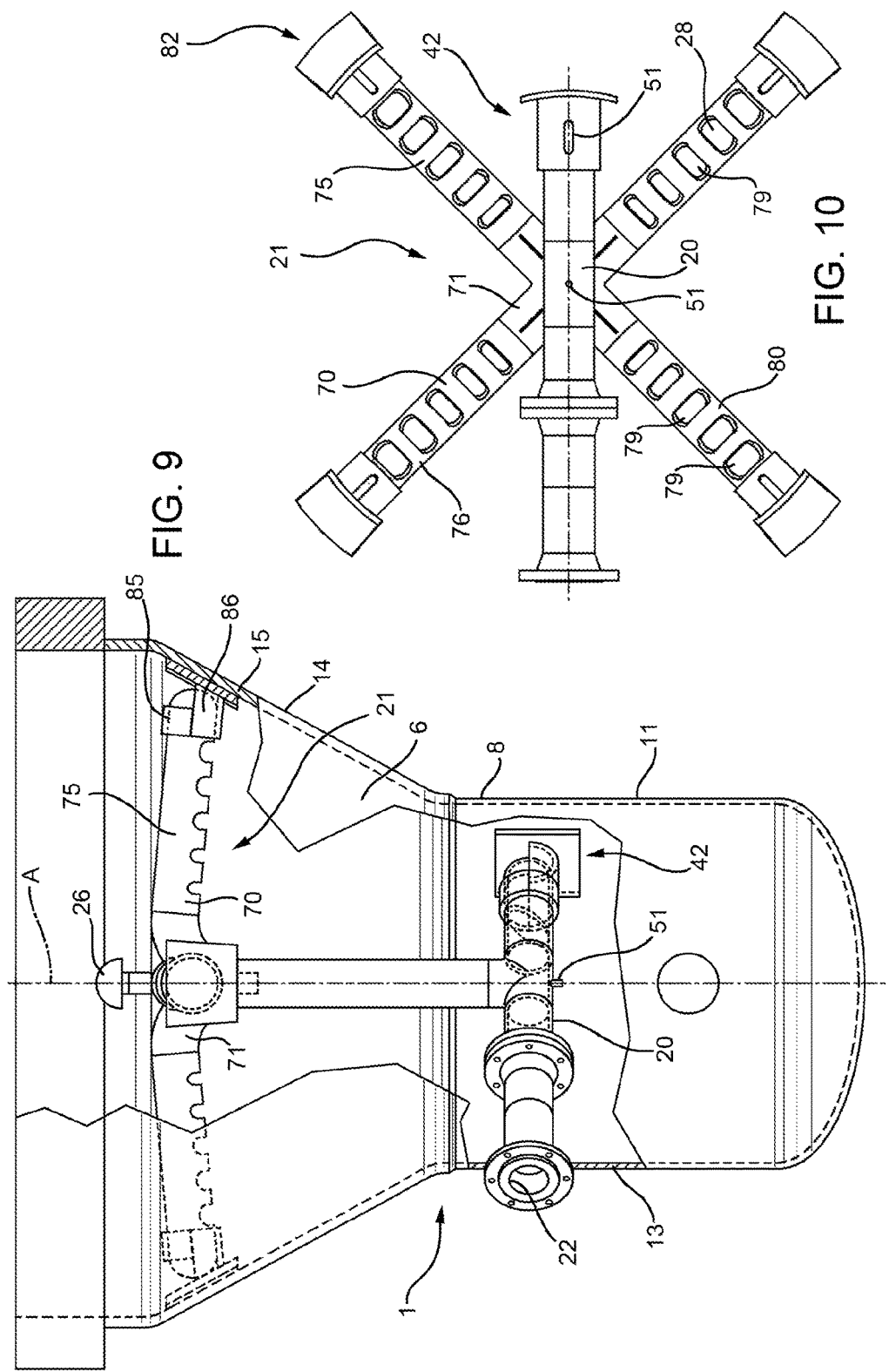

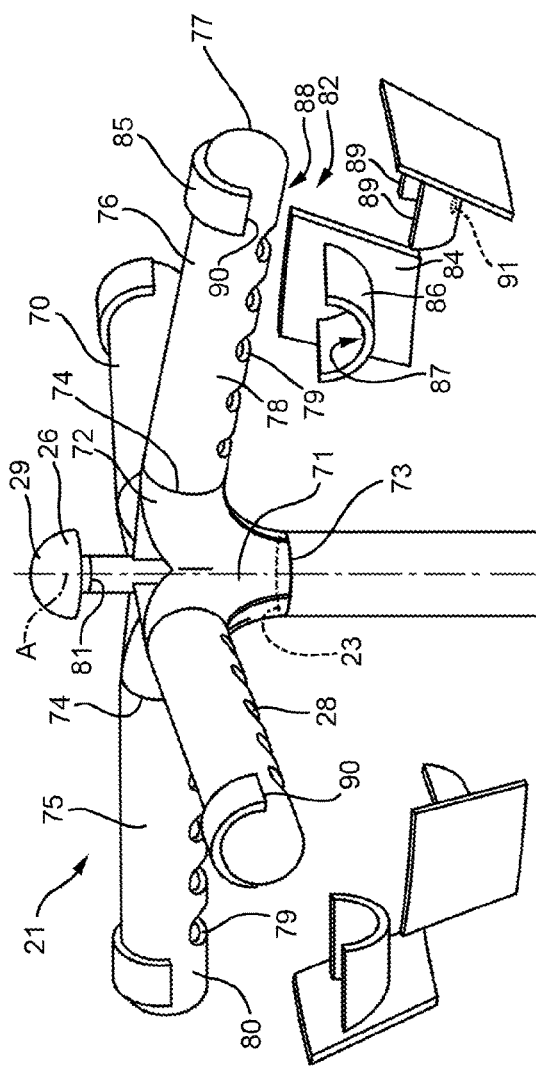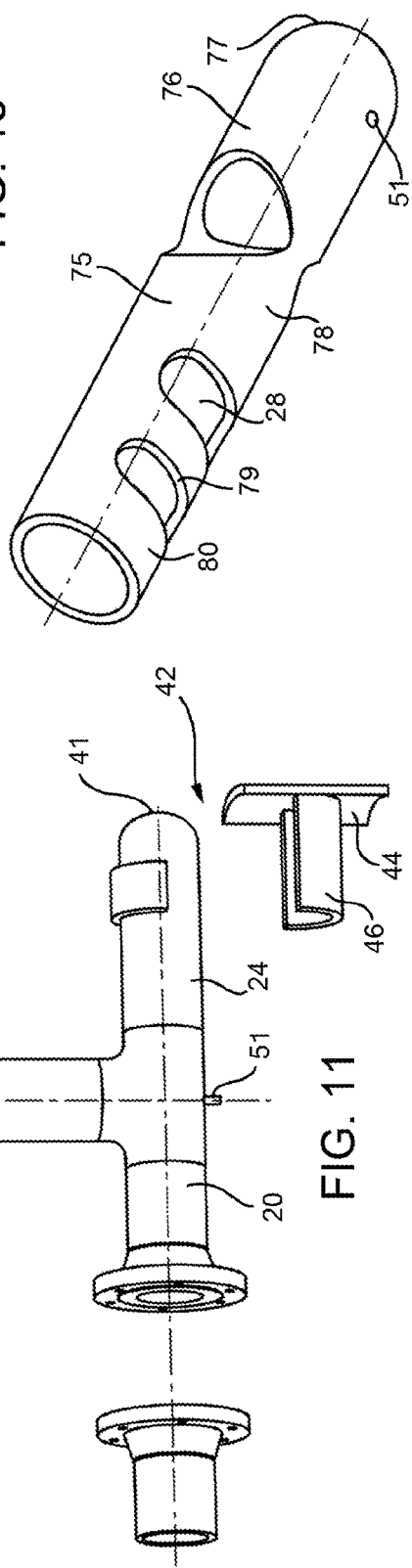

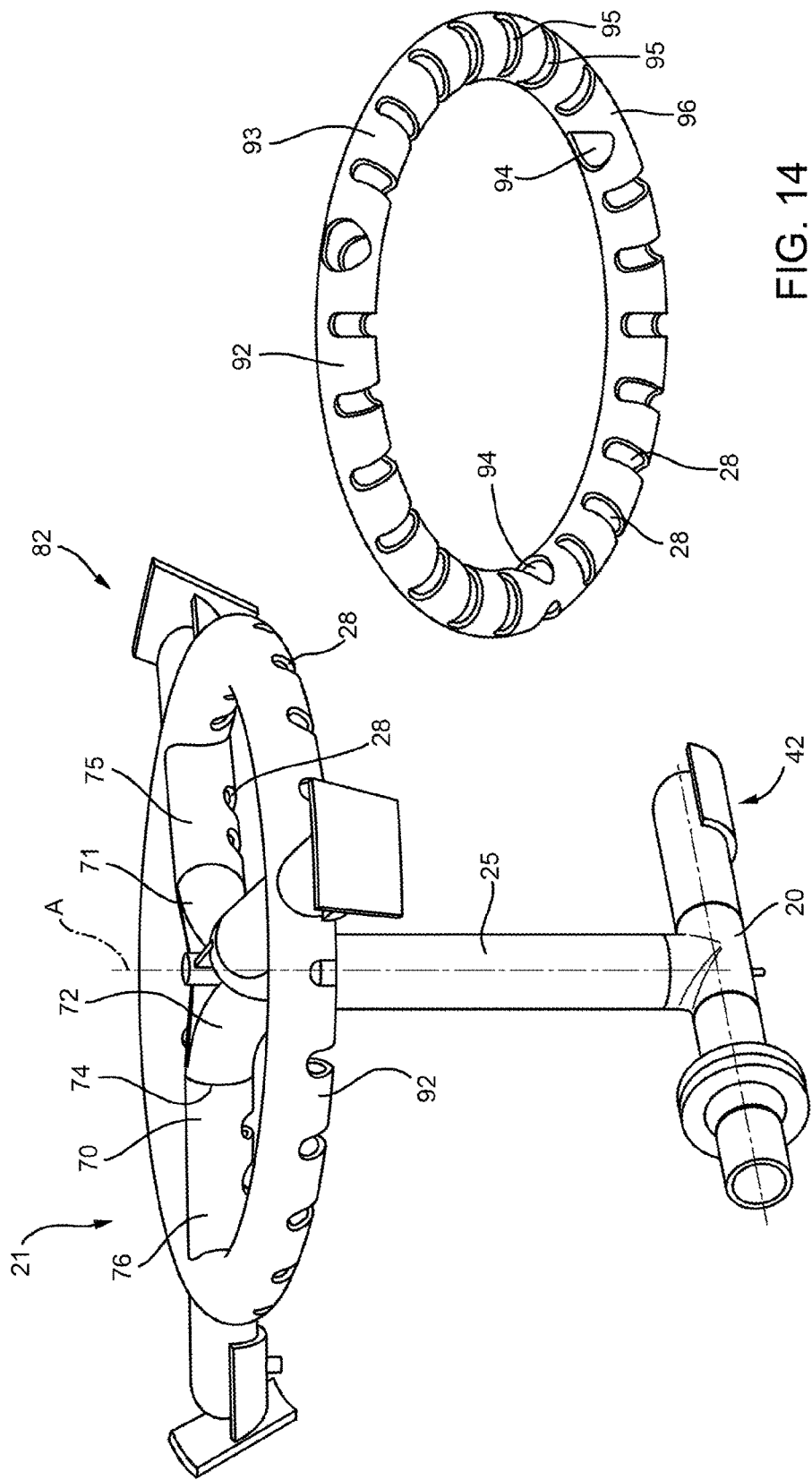

GAS DIFFUSION SYSTEM AND METHOD FOR INTRODUCING A GAS STREAM IN AN APPARATUS, IN PARTICULAR A PASSIVATING GAS STREAM IN A UREA PLANT

PRIORITY CLAIM

This application is a national stage application of PCT/IB2014/062877, filed on Jul. 4, 2014, now WO 2015/001536, which claims the benefit of and priority to Italian Patent Application No. MI2013A 001139, filed on Jul. 5, 2013, the entire contents of which are each incorporated by reference herein.

BACKGROUND

As is known, urea is produced industrially using processes based on the high-temperature, high-pressure reaction of carbon dioxide and ammonia to form ammonium carbamate, and on the subsequent decomposition reaction of ammonium carbamate to form urea; the resulting urea solution is then concentrated gradually to recover the non-converted reagents; and, finally, the urea is solidified in the form of granules or prills.

In a typical plant for production of urea (i.e., a urea plant), the various stages in the process are conducted in a high-pressure section, which also has a synthesis reactor where the ammonia reacts with the carbon dioxide, a medium-pressure section, and a low-pressure section, with respective decomposers configured to decompose ammonium carbamate into urea.

Because the carbon dioxide-ammonia reaction, mainly due to the intervening ammonium carbamate, severely corrodes the stainless steel which the urea plant component parts are normally made of, some urea production processes employ passivating oxygen. That is, a gas stream containing oxygen is injected at predetermined points along the plant to passivate the metal (typically stainless steel) surfaces of the plant to prevent or reduce corrosion.

For example, a passivating oxygen-containing gas stream is fed into the medium-pressure section decomposer.

FIG. 1 shows a simplified schematic of the bottom part of a known urea plant decomposition apparatus (decomposer) 2.

Basically, decomposer 2 extends along a vertical axis A, and comprises an outer casing 4 extending about axis A and housing a pipe bundle 5 (only shown partly) between a top chamber (not shown in FIG. 1) and a bottom chamber 6.

Pipe bundle 5 is supported on a bottom pipe plate 7 and a top pipe plate (not shown in FIG. 1).

Bottom chamber 6 is located beneath pipe plate 7 and is bounded by a container or so-called 'holder' 8 located beneath pipe plate 7 and extending along axis A, between a bottom end 9 and a top end 10 connected to casing 4.

Holder 8 substantially flares upwards and comprises in particular a bottom catch portion 11 closed underneath by a bottom (e.g., concave) wall 12 and having a substantially cylindrical lateral wall 13 around axis A; and a funnel-shaped, upward-flaring top diffusion portion 14 having a truncated-cone-shaped lateral wall 15 around axis A.

Holder 8 has a liquid-phase outlet 16 (for the liquid phase which collects in catch portion 11 at the bottom of holder 8) located close to bottom wall 12 and through lateral wall 13; and a gaseous-phase inlet 17 located through lateral wall 13 just above the level of the liquid collected in catch portion 11 and just below the start of diffusion portion 14. Inlet 17 projects from lateral wall 13 into chamber 6, and has an upward-sloping open free end.

Inlet 17 is where the passivating gas stream is fed into decomposer 2.

Despite the passivating gas stream, however, significant corrosion is still observed, especially in the medium-pressure section decomposer.

Moreover, known decomposers, and more specifically the gas stream inlets employed in them, also pose problems in connection with the configuration of the inlets.

More specifically, as configured, certain known inlets enable the corrosive urea/carbamate mixture percolating downwards (from the pipe bundle) to enter and settle and so potentially deteriorate the material the inlet is made of.

Because of the location of the inlets—usually just above the level of the liquid accumulated at the bottom of the decomposer—an increase in the liquid level (e.g., caused by excess production), may partly or completely submerge the inlet, thus preventing the inlet from operating properly. And since known inlets have no provision for drainage, any liquid inside them cannot be removed. In other words, known decomposers of the above type are not without certain drawbacks.

SUMMARY

The present disclosure relates to a gas diffusion system and method configured to feed a gas stream, in particular a passivating gas stream, into an apparatus, in particular a decomposer, of a urea plant (i.e., a urea production plant).

More specifically, the present disclosure relates to a gas diffusion system and method configured to feed a passivating gas stream into a urea plant decomposer (e.g., into the decomposer of a medium-pressure section of the urea plant).

The present disclosure also relates to a urea plant apparatus equipped with a gas diffusion system and/or implementing such a method.

It is therefore an advantage of the present disclosure to provide a gas diffusion system and method configured to eliminate certain of the above drawbacks of certain of the known art. More specifically, it is an advantage of the present disclosure to provide a system and method configured to eliminate or reduce corrosion phenomena.

According to the present disclosure, there are provided a gas diffusion system and method configured to feed a gas stream, in particular a passivating gas stream, into an apparatus, in particular a decomposer, of a urea plant.

In one such embodiment, the present disclosure includes a urea plant decomposer with a gas diffusion system configured to feed a passivating gas stream into the urea plant decomposer extending along an axis. The urea plant decomposer includes a bottom holder which defines a chamber, the bottom holder including: a bottom portion of a casing, a bottom catch portion closed at a bottom end by a bottom wall, and having a substantially cylindrical lateral wall around the axis, and a funnel-shaped top diffusion portion which flares upwards, tapers towards the bottom catch portion and is bounded by a truncated-cone-shaped lateral wall around the axis. The urea plant decomposer includes a gas feed conduit including: a base pipe transverse to the substantially cylindrical lateral wall and the axis, and a fitting which terminates with an opening defining an outlet which is transverse to the axis and from which the passivating gas stream flows substantially parallel to the axis, the outlet being located centrally inside the bottom holder and the defined chamber substantially about the axis, wherein the gas feed conduit projects inside the chamber from an inlet hole formed through the substantially cylindrical lateral wall of the bottom catch portion and the gas feed conduit terminates with the outlet. The urea plant decomposer includes a diffuser assembly configured to diffuse the passivating gas stream from the gas feed conduit inside the chamber, the diffuser assembly being shaped to: intercept the passivating gas stream flowing axially from the outlet, and divert the passivating gas stream substantially radially with respect to the axis and about the axis.

In another such embodiment, the present disclosure includes a method for feeding a passivating gas stream into a decomposer of a urea plant. The method includes feeding the passivating gas stream into the decomposer along a conduit having an outlet from which the passivating gas stream flows in a substantially axial direction, parallel to a vertical axis, the passivating gas stream being fed into a chamber defined by a bottom holder which includes a bottom portion of a casing of the decomposer and includes a bottom catch portion closed at a bottom end by a bottom wall and having a substantially cylindrical lateral wall around the axis and a funnel-shaped top diffusion portion which flares upwards, and tapers towards the catch portion and is bounded by a truncated-cone-shaped lateral wall around the axis, the conduit projecting inside the chamber from an inlet hole formed through the lateral wall of the bottom catch portion and terminating with the outlet, the conduit including a base pipe transverse to the substantially cylindrical lateral wall and the axis and a fitting which terminates with an opening defining the outlet and which is transverse to the axis and which is located centrally inside the bottom holder and the chamber substantially about the axis. The method also includes intercepting the passivating gas stream flowing axially from the outlet, and diverting the passivating gas stream substantially radially with respect to the axis and about the axis via a diffuser assembly.

Research by the Applicant has led to the conclusion that the corrosion phenomena encountered, despite the use of passivating gas, in certain parts of the urea plant, and more specifically in the decomposers into which passivating gas is fed directly, are mainly due to poor and/or uneven distribution of the gas, thus resulting in blind areas where material (e.g., in the case of decomposers, the material of the pipe bundle and plate) is left untreated.

In other words, research by the Applicant shows that the way in which passivating gas is currently injected into decomposers (but also into other parts of the urea plant) fails to distribute the gas uniformly over the entire contact area, thus enabling corrosion phenomena to develop.

In decomposers specifically, research by the Applicant also shows poor distribution of the gaseous phase inside the pipe bundle over the gas inlet, thus reducing the chemical reaction efficiency of the process.

Using a new type of gas diffusion system, on the other hand, the present disclosure provides for uniformly distributing the passivating gas. In other words, the present disclosure provides uniform distribution of the passivating gas stream to passivate the entire area (or substantially the entire area) involved, and also uniform supply to the vertical pipes, so relatively cheaper materials can be used to reduce the cost of the decomposer.

The present disclosure also prevents the corrosive mixture inside the decomposer from penetrating and/or remaining inside, and possibly deteriorating the material of, the gas diffusion system, by preventing it from percolating downwards, by preventing an increase in the level of the mixture collected at the bottom of the decomposer, and at any rate by enabling drainage of any liquid penetrating the gas diffusion system.

The present disclosure also has the following additional advantages:

compact diffuser assembly for relatively easy transport and relatively easy installation, even on existing plants;

relatively easy-to-make, relatively easy-to-assemble diffuser assembly;

modular system configuration to adapt to different configurations;

relatively extremely simple, highly effective mechanical supports capable of withstanding static and dynamic load conditions, especially thermal gradients and gas-injection-induced dynamic forces;

self-draining capability, to prevent liquids from settling and hardening and so clogging the passivating gas outlet holes;

outlet hole arrangement configured to ensure gas distribution to process requirements, and good overall passivation of the whole area involved (plate and pipe bundle);

reduced passivating gas speed vector; and selectable gas outlet hole size, to prevent the hardened deposited liquid from clogging the outlet holes.

Additional features and advantages are described in, and will be apparent from the following Detailed Description and the figures.

BRIEF DESCRIPTION OF THE DRAWINGS

A number of non-limiting embodiments of the present disclosure will be described by way of example with reference to the attached drawings, in which:

FIG. 1 shows a partial schematic longitudinal section of the bottom part of a urea plant apparatus, in particular a urea plant medium-pressure section decomposer, equipped with a gaseous-phase inlet of a known configuration;

FIG. 2 shows a schematic, partly longitudinally sectioned side view of a gas diffusion device in accordance with a first embodiment of the present disclosure and integrated in the bottom part of a urea plant apparatus, in particular a urea plant medium-pressure section decomposer;

FIGS. 3 and 4 show views in perspective of respective component parts of the FIG. 2 gad diffusion device;

FIG. 5 shows a schematic, partly longitudinally sectioned side view of a gas diffusion device in accordance with a second embodiment of the present disclosure;

FIG. 6 shows a side view of a detail of the FIG. 5 gas diffusion device;

FIG. 9 shows a schematic, partly longitudinally sectioned side view of a gas diffusion device in accordance with a third embodiment of the present disclosure;

FIG. 10 shows an underside plan view, with parts removed for clarity, of a component part of the FIG. 9 gas diffusion device;

FIG. 11 shows a partly exploded view in perspective, with parts removed for clarity, of the FIG. 10 component;

FIG. 12 shows a view in perspective of a variation of the FIG. 11 component part in accordance with a fourth embodiment of the present disclosure; and FIGS. 13 and 14 show views in perspective of respective details of the FIG. 12 component.

DETAILED DESCRIPTION

Figure 7:
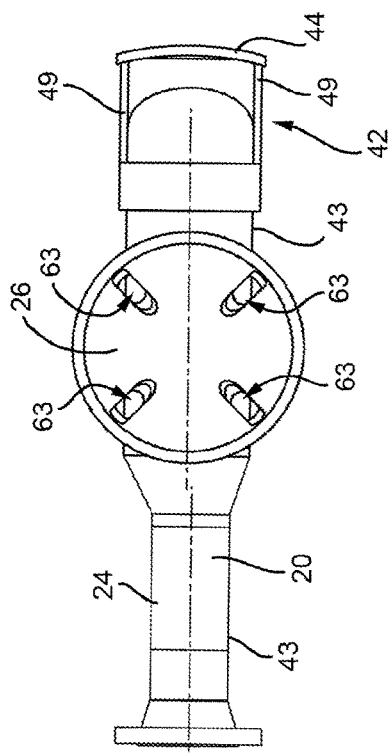
FIG. 7 shows a top plan view, with parts removed for clarity, of the FIG. 6 detail.
Figure 8:
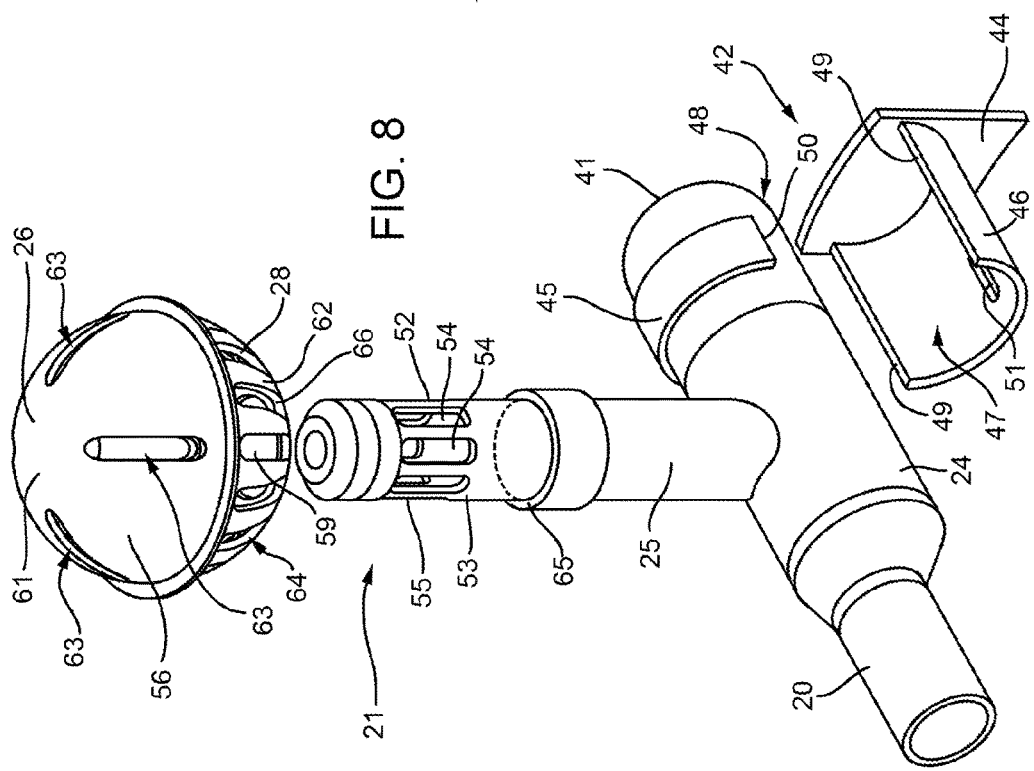
FIG. 8 shows an exploded view in perspective, with parts removed for clarity, of the FIG. 6 detail.

Referring now to the example embodiments of the present disclosure illustrated in FIGS. 1 to 14, number 1 in FIG. 2 indicates as a whole a gas diffusion system of a urea plant apparatus 2, in particular a urea plant medium-pressure section decomposer of the type described with reference to FIG. 1, and of which FIG. 2 only shows a bottom part 3 in which gas diffusion system 1 is integrated.

As stated with reference to FIG. 1, but not shown in FIG. 2 for the sake of simplicity, apparatus 2 basically comprises an outer casing 4 housing a pipe bundle, supported by a bottom pipe plate and a top pipe plate and located between a top chamber and a bottom chamber 6.

Casing 4 is connected to a bottom holder 8, which constitutes a bottom portion of casing 4 and defines a chamber 6 (constituting the bottom chamber of apparatus 2, beneath the bottom pipe plate), equipped with inlets/outlets (shown in FIG. 1 but not in FIG. 2 for the sake of simplicity) required for the operation of apparatus 2 and which include a liquid-phase outlet (not shown) for the liquid phase collected at the bottom of apparatus 2 (i.e., the bottom of chamber 6).

Holder 8 extends along an axis A between a bottom end 9 and a top end 10, connected to casing 4.

Holder 8 comprises a bottom catch portion 11 closed at bottom end 9 by a bottom (e.g., concave) wall 12 and having a substantially cylindrical lateral wall 13 around axis A; and a funnel-shaped top diffusion portion 14 which generically flares (i.e., diverges) upwards, tapers towards catch portion 11, and is bounded by a truncated-cone-shaped lateral wall 15 around axis A.

Catch portion 11 and diffusion portion 14 are connected along an annular joint 18.

System 1 is located inside holder 8 and comprises a gas feed conduit 20, which feeds a gas stream into apparatus 2 and, more specifically, into holder 8 (i.e., into chamber 6); and a diffuser assembly 21 which diffuses the gas supplied from conduit 20 inside chamber 6 and, more specifically, towards top end 10 of holder 8.

Conduit 20 projects inside chamber 6 from an inlet hole 22, formed through lateral wall 13 of portion 11, and terminates with an outlet 23. In the non-limiting example in FIG. 2, conduit 20 comprises a base pipe 24 substantially perpendicular to lateral wall 13 and axis A; and a fitting 25 (e.g., an elbow (90°) fitting), which terminates with an opening defining outlet 23, which is substantially perpendicular to axis A and located centrally inside holder 8 and chamber 6, substantially about axis A.

Diffuser assembly 21 comprises a central diffuser 26 and, in certain embodiments, an optional peripheral shield 27, which are located at respective axially opposite ends of diffusion portion 14, are spaced axially part along axis A, and are offset radially with respect to each other. More specifically, diffuser 26 is located substantially on a level with joint 18, and shield 27 is located at end 10 and radially outwards with respect to diffuser 26.

Diffuser assembly 21 is shaped so as to intercept the gas stream flowing axially (parallel to axis A) from outlet 23, and divert the gas stream substantially radially with respect to axis A (i.e., crosswise to axis A) and uniformly about axis A through a plurality of gas outlet openings 28 arranged about axis A.

More specifically, diffuser 26 is located at and over outlet 23 of conduit 20, is aligned with outlet 23 along axis A, is positioned crosswise to and substantially around axis A, and is transversely larger than outlet 23 (i.e., the projection of diffuser 26 in a plane perpendicular to axis A is larger in area than the opening defining outlet 23) so as to prevent the gas stream from outlet 23 from flowing along axis A.

With reference also to FIG. 3, diffuser 26 comprises a hood 29 which intercepts the gas stream axially and has radial gas outlet openings 28 equally spaced about axis A and through which the gas stream intercepted by hood 29 flows.

Hood 29, for example, is dome-shaped, and has a concave inner surface 30 facing outlet 23; a convex outer surface 31 opposite surface 30; and a peripheral edge 32 spaced axially apart from, and radially outwards of outlet 23.

Hood 29 is supported by supporting arms 33, which project (e.g., substantially vertically or at an angle to axis A) from a fastening ring 34 fixed to conduit 20. Supporting arms 33 are regularly and angularly spaced about axis A and define openings 28.

Shield 27 is located at top end 10 of holder 8 and fixed to truncated-cone-shaped lateral wall 15 of diffusion portion 14. More specifically, shield 27 projects radially from lateral wall 15 into diffusion portion 14.

With reference also to FIG. 4, shield 27 comprises an annular member 36 about axis A and having a plurality of peripheral through openings 37 equally spaced angularly about axis A. More specifically, annular member 36 has a substantially circular, radially inner peripheral edge 38; and a radially outer peripheral edge 39 which contacts lateral wall 15 and has peripheral slots formed in edge 39, spaced angularly apart along edge 39, and defining openings 37. Annular member 36 tapers upwards (towards end 10) from edge 39 to edge 38, so that openings 37 slope with respect to axis A.

In actual use, system 1 implements the method according to the present disclosure as follows.

System 1 feeds a passivating (oxygen-containing) gas stream into apparatus 2. The gas stream flows into apparatus 2 along conduit 20, and flows out from outlet 23 in a substantially axial direction (i.e., parallel to vertical axis A).

The gas stream is intercepted and diffused inside chamber 6 by diffuser 26. More specifically, the gas stream from outlet 23 is intercepted by hood 29, which diverts the gas stream radially and distributes the gas stream through openings 28. As the gas stream flows radially out of openings 28, the gas stream once more flows upwards inside chamber 6 and is distributed further through openings 37 in shield 27.

In the FIG. 5-8 embodiment, too, in which details similar or identical to those already described are indicated using the same reference numbers, system 1 comprises a gas feed conduit 20 which projects inside chamber 6 from an inlet hole 22 through lateral wall 13 of catch portion 11, and terminates with an outlet 23; and a diffuser assembly 21 configured to diffuse the gas supplied through conduit 20 inside chamber 6.

Conduit 20 extends substantially perpendicular to axis A, and diametrically across holder 8, inside chamber 6, between inlet hole 22 and a dead (i.e., closed) end 41 with a mechanical support 42 connecting end 41 to lateral wall 13.

Conduit 20 is substantially T-shaped, and comprises a base pipe 24 substantially perpendicular to lateral wall 13 and axis A; and a fitting 25 perpendicular to the base pipe and parallel to axis A. Fitting 25 is located centrally inside chamber 6, substantially along axis A, and terminates with an opening defining outlet 23. Outlet 23 is substantially perpendicular to axis A and is located centrally inside holder 8 and chamber 6, about axis A.

As shown in FIGS. 5-8, base pipe 24 optionally comprises two or more portions 43 of different cross sections and/or eccentric with respect to one another.

Support 42 comprises a plate 44, fixed to (e.g., welded or simply contacting) lateral wall 13; and a fastener 45, fixed to end 41 of conduit 20. Plate 44 has a curved, saddle-like bracket 46 which projects from lateral wall 13 and has a half-shell seat 47 shaped so as to accommodate a bottom end portion 48 of conduit 20 and having two opposite lateral edges 49. Fastener 45 is fixed over conduit 20, and has two downward-facing lateral shoulders 50. Bottom end portion 48 of conduit 20 simply rests on seat 47. When bottom end portion 48 of conduit 20 is seated inside seat 47, conduit 20 is supported axially by plate 44 (more specifically, by bracket 46), is free to slide longitudinally inside seat 47, but is locked angularly (to prevent conduit from rotating about its longitudinal axis) by shoulders 50 of fastener 45 engaging lateral edges 49. An optional damping panel (not shown) is inserted between seat 47 and portion 48 to reduce gas flow-induced vibration and dissipate dynamic energy produced by fluid-dynamic forces.

Seat 47 has at least one drain hole 51 formed through saddle 46, at the bottom of seat 47, to drain off any liquid collected inside seat 47.

Further drain holes 51 are formed on diffuser assembly 21 (e.g., in bottom end portion 48, to drain off any liquid penetrating diffuser assembly 21).

Diffuser assembly 21 is shaped so as to intercept the gas stream flowing axially (parallel to axis A) from outlet 23, and divert the gas stream substantially radially with respect to axis A (i.e., crosswise to axis A) and uniformly about axis A.

More specifically, diffuser assembly 21 has a plurality of gas outlet openings 28 distributed about axis A and in the form of slots elongated longitudinally in a main direction.

More specifically, diffuser assembly 21 comprises a central diffuser 26 associated with an axial distributor 52, which receives the gas stream from outlet 23 of conduit 20 and distributes the gas stream radially to diffuser 26.

Distributor 52 is located at and over outlet 23 of conduit 20, is aligned with outlet 23 along axis A, is connected to fitting 25, and extends from fitting 25 along (or parallel to) axis A.

More specifically, distributor 52 comprises a tubular member 53 which extends along axis A and has a plurality of longitudinal slits 54 formed through the lateral wall 55 of member 53 and parallel to one another and to axis A. Slits 54 are equally spaced angularly about axis A and elongated parallel to axis A.

Diffuser 26 surrounds distributor 52 along axis A. More specifically, diffuser 26 comprises a hollow body 56—for example, but not necessarily, substantially spherical—having an inner seat 57, bounded by a wall 58 which surrounds the top of distributor 52 radially (about axis A). Distributor 52 is housed inside seat 57 and fitted through a bottom opening 59 in wall 58, with slits 54 housed entirely inside diffuser 26 and surrounded by wall 58.

Body 56 comprises, for example, a top dome-shaped portion 61 and an opposite bottom dome-shaped portion 62, which, for example, are substantially hemispherical and joined along a horizontal centreline plane of body 56.

Diffuser 26 has a plurality of radial openings 28 formed through wall 58 and defined by respective vertically elongated slots equally spaced about axis A. More specifically, diffuser 26 has a first set of slots 63, formed in top dome-shaped portion 61 of body 56 above the horizontal centreline plane of body 56 and equally spaced angularly about axis A; and a second set of slots 64, formed in bottom dome-shaped portion 62 below the horizontal centreline plane of body 56 and equally spaced angularly about axis A.

In the FIG. 5-8 example, slots 64 outnumber slots 63.

Diffuser 26 is fitted about tubular member 53 and is supported axially, for example, by a radially outer flange 65 connecting distributor 52 to fitting 25. Diffuser 26 rests on flange 65 by an edge 66 bounding opening 59.

Conduit 20 and, more specifically, fitting 25 are dimensioned so that diffuser 26 is located inside diffusion portion 14 above joint 18.

Implementing the method according to the present disclosure, system 1 feeds a passivating (oxygen-containing) gas stream into apparatus 2. The gas stream flows into apparatus 2 along conduit 20, and flows out from outlet 23 in a substantially axial direction (i.e., parallel to vertical axis A).

The gas stream is intercepted and diffused inside chamber 6 by diffuser assembly 21. More specifically, the gas stream from outlet 23 is intercepted by distributor 52, which diverts the gas stream radially and distributes the gas stream through slits 54. As the gas stream flows radially out of slits 54, the gas stream then flows through slots 63 and 64 and once more upwards inside chamber 6, and more specifically inside diffusion portion 14.

In the FIG. 9-11 embodiment, in which details similar or identical to those already described are indicated using the same reference numbers, system 1 again comprises a gas feed conduit 20 (similar to the one described with reference to FIGS. 5-8), and a diffuser assembly 21.

Conduit 20 again projects inside chamber 6 from inlet hole 22 (formed through lateral wall 13 of catch portion 11) and terminates with outlet 23. Conduit 20 extends substantially perpendicular to axis A, and diametrically across holder 8, inside chamber 6, between inlet hole 22 and dead (i.e., closed) end 41 with mechanical support 42 (such as of the type described with reference to FIGS. 5-8).

In this embodiment, too, conduit 20 is substantially T-shaped, and comprises a base pipe 24 substantially perpendicular to lateral wall 13 and axis A; and a fitting 25 perpendicular to the base pipe and parallel to axis A. Fitting 25 is located centrally inside chamber 6, substantially along axis A, and terminates with an opening defining outlet 23 substantially perpendicular to axis A and located centrally inside holder 8 and chamber 6, about axis A.

Diffuser assembly 21 is again shaped so as to intercept the gas stream flowing axially (i.e., parallel to axis A) from outlet 23, and divert the gas stream substantially radially with respect to axis A (i.e., crosswise to axis A) and uniformly about axis A.

Diffuser assembly 21 again has a plurality of gas outlet openings 28 distributed about axis A and in the form of slots elongated longitudinally in a main direction. In this embodiment, diffuser assembly 21 has gas outlet openings 28 at different distances from axis A.

In this embodiment, diffuser assembly 21 comprises a main radial diffuser 70 associated with a radial distributor 71, which receives the gas stream from outlet 23 of conduit 20 and distributes the gas stream radially to diffuser 70; and an optional additional central diffuser 26.

Distributor 71 is located at and over outlet 23 of conduit 20, is aligned with outlet 23 along axis A, is connected to fitting 25, and extends from fitting 25 along (or parallel to) axis A.

More specifically, distributor 71 comprises a body 72 having an axial inlet 73, aligned along axis A and communicating with outlet 23; and a plurality of (e.g., four) radial outlets 74 angularly spaced and uniformly distributed about axis A.

Diffuser 70 comprises a plurality of arms 75 equally spaced about axis A, projecting radially from body 72 of distributor 71, and connected to respective outlets 74.

Each arm 75 comprises a tubular member 76 which extends radially from body 72 towards a closed end 77, and has a plurality of bottom, downward-facing openings 28 formed through the lateral wall 78 of tubular member 76.

More specifically, openings 28 are defined by respective slots 79 spaced axially apart along arm 75 and located on a bottom portion 80 of arm 75, beneath a horizontal centreline plane of tubular member 76.

Slots 79 are elongated crosswise to arm 75 (i.e., are oriented with their larger dimension, or length, perpendicular to arm 75, and their smaller dimension, or width, along arm 75).

In certain embodiments, slots 79 increase in area along arm 75, towards closed end 77, having for example the same length (measured crosswise to arm 75) and increasing width (measured along arm 75).

In certain embodiments, arms 75 slope downwards towards respective ends 77, and are supported at respective ends 77 by mechanical supports 82 similar to support 42 supporting end 41 of conduit 20.

Each support 82 therefore also comprises a plate 84, fixed to (e.g., welded or simply contacting) holder 8, and more specifically lateral wall 15 of diffusion portion 14; and a fastener 85, fixed to end 77 of an arm 75. Plate 84 has a curved, saddle-like bracket 86 which projects from lateral wall 15 and has a half-shell seat 87 shaped so as to accommodate a bottom end portion 88 of arm 75 and having two opposite lateral edges 89. Fastener 85 is fixed over arm 75, and has two downward-facing lateral shoulders 90. Bottom end portion 88 of each arm 75 simply rests on respective seat 87. When bottom end portion 88 of arm 75 is seated inside seat 87, arm 75 is supported axially by plate 84 (more specifically, by bracket 86), is free to slide longitudinally inside seat 87, but is locked angularly (to prevent the arm from rotating about its longitudinal axis) by shoulders 90 of fastener 85 engaging lateral edges 89. An optional damping panel (not shown) is inserted between each seat 87 and respective portion 88 housed in seat 87, to reduce gas flow-induced vibration and dissipate dynamic energy produced by fluid-dynamic forces.

In this embodiment, too, diffuser assembly 21 has one or more drain holes 51 formed, in particular, in seat 47 of support 42 and/or in bottom end portion 48 of conduit 20.

Further drain holes 91 are formed in seats 87 of supports 82 and/or in bottom end portions 88 of arms 75.

Conduit 20 and, more specifically, fitting 25 are dimensioned so as diffuser 70 is located in diffusion portion 14, close to end 10.

Additional central diffuser 26 is similar to the one described with reference to FIGS. 2 and 3.

If additional central diffuser 26 is provided, distributor 71 comprises a further top axial outlet along axis A and defining an auxiliary outlet opening 81. Diffuser 26 is located over opening 81, is aligned with opening 81 along axis A, is positioned crosswise to and substantially around axis A, and is transversely larger than opening 81, so as to prevent the gas stream from opening 81 from flowing along axis A.

As described previously, diffuser 26 comprises a hood 29 (e.g., dome-shaped) which intercepts the gas stream axially and has radial openings 28 (not shown in FIGS. 9-11) through which the gas stream intercepted by hood 29 flows.

In actual use, the gas stream flows into apparatus 2 along conduit 20, and flows out from outlet 23 in a substantially axial direction (i.e., parallel to vertical axis A).

The gas stream is intercepted and diffused inside chamber 6 by diffuser assembly 21. More specifically, the gas stream from outlet 23 is intercepted by distributor 71, which diverts the gas stream radially and distributes the gas stream through outlets 74 into arms 75, from which the gas stream flows out through slots 79 and once more upwards inside diffusion portion 14 of chamber 6.

Part of the gas stream may also flow through opening 81, and is diverted by additional central diffuser 26.

In the FIG. 12-14 embodiment, in which details similar or identical to those already described are indicated using the same reference numbers, system 1 again comprises a gas feed conduit 20 and a diffuser assembly 21.

Conduit 20 is similar to the one described with reference to FIGS. 9-11.

In the FIG. 12-14 embodiment, diffuser assembly 21 comprises a first radial diffuser 70 associated with a radial distributor 71; and a second annular central diffuser 92 connected to first diffuser 70.

As in the FIG. 9-11 embodiment, distributor 71 is located at and over outlet 23 of conduit 20, and is aligned with outlet 23 along axis A to receive the gas stream from outlet 23 of conduit 20 and distribute the gas stream radially to diffuser 70.

More specifically, distributor 71 is connected to fitting 25, and extends from fitting 25 along (or parallel to) axis A; distributor 71 comprises a body 72 having an axial inlet 73, aligned along axis A and communicating with outlet 23; and a plurality of (e.g., three) radial outlets 74 equally spaced angularly about axis A.

Diffuser 70 comprises a plurality of arms 75 projecting radially from body 72 of distributor 71, and connected to respective outlets 74.

Each arm 75 comprises a tubular member 76 which extends radially from body 72 towards a closed end 77, and has a plurality of bottom, downward-facing openings 28 formed through the lateral wall 78 of tubular member 76.

More specifically, openings 28 are defined by respective slots 79 spaced axially apart along arm 75 and located on a bottom portion 80 of arm 75, beneath a horizontal centreline plane of tubular member 76.

Slots 79 are elongated crosswise to arm 75 (i.e., are oriented with their larger dimension, or length, perpendicular to arm 75, and their smaller dimension, or width, along arm 75).

Diffuser 92 is ring-shaped about axis A.

More specifically, diffuser 92 comprises a hollow toroidal body 93 having a plurality of inlets 94 spaced angularly apart, facing axis A, and connected to respective arms 75 of diffuser 70.

Body 93 has a plurality of downward-facing bottom openings 28 formed through the lateral wall 78 of body 93.

More specifically, openings 28 are defined by respective slots 95 spaced circumferentially apart along body 93 and located on a bottom portion 96 of body 93, beneath a horizontal centreline plane of body 93.

Slots 95 are elongated radially with respect to axis A and crosswise with respect to body 93.

Diffuser 92 is advantageously supported by mechanical supports 82 similar to the ones described for supporting arms 75.

In actual use, the gas stream flows into apparatus 2 along conduit 20, and flows out from outlet 23 in a substantially axial direction (i.e., parallel to vertical axis A).

The gas stream is intercepted and diffused inside chamber 6 by diffuser assembly 21. More specifically, the gas stream from outlet 23 is intercepted by distributor 71, which diverts the gas stream radially and distributes the gas stream through outlets 74 into arms 75.

Part of the gas stream flows out of arms 75 through slots 79, and then up again inside diffusion portion 14 of chamber 6; whereas another part of the gas stream flows along arms 75 into diffuser 92 and out through slots 95.

The solutions described in the above embodiments of the present disclosure may be variously combined.

Clearly, other changes may be made to the system and method as described and illustrated herein without, however, departing from the scope of the accompanying Claims. Accordingly, various changes and modifications to the presently disclosed embodiments will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A urea plant decomposer with a gas diffusion system configured to feed a passivating gas stream into the urea plant decomposer extending along an axis, said urea plant decomposer comprising:
   a bottom holder which defines a chamber, said bottom holder including:
      a bottom portion of a casing,
      a bottom catch portion closed at a bottom end by a bottom wall, and having a substantially cylindrical lateral wall around the axis, and
      a funnel-shaped top diffusion portion which flares upwards, tapers towards the bottom catch portion and is bounded by a truncated-cone-shaped lateral wall around the axis;
   a gas feed conduit including:
      a base pipe transverse to the substantially cylindrical lateral wall and the axis, and
      a fitting which terminates with an opening defining an outlet which is transverse to the axis and from which the passivating gas stream flows substantially parallel to the axis, said outlet being located centrally inside the bottom holder and the defined chamber substantially about the axis, wherein said gas feed conduit projects inside the chamber from an inlet hole formed through the substantially cylindrical lateral wall of the bottom catch portion and said gas feed conduit terminates with said outlet; and
   a diffuser assembly including a central diffuser and a peripheral shield which are spaced axially apart along the axis and offset radially with respect to each other, wherein the peripheral shield includes an annular member positioned about the axis and defining a plurality of through peripheral openings, angularly spaced apart from one another and uniformly distributed around the axis, and the diffuser assembly is configured to diffuse the passivating gas stream from the gas feed conduit inside the chamber, said diffuser assembly being shaped to:
      intercept the passivating gas stream flowing axially from the outlet, and
      divert the passivating gas stream substantially radially with respect to the axis and about the axis.

2. The urea plant decomposer of claim 1, wherein the diffuser assembly defines a plurality of gas outlet openings arranged about the axis.

3. The urea plant decomposer of claim 2, wherein at least two of the plurality of gas outlet openings are at different distances from the axis.

4. The urea plant decomposer of claim 2, wherein the gas outlet openings define slots elongated longitudinally in a first direction.

5. The urea plant decomposer of claim 1, wherein the annular member has a radially inner peripheral edge and a radially outer peripheral edge which define a plurality of peripheral slots spaced angularly apart and defining the peripheral openings.

6. The urea plant decomposer of claim 1, wherein the annular member tapers upwards from the radially outer peripheral edge to the radially inner peripheral edge.

7. The urea plant decomposer of claim 1, wherein the fitting projects perpendicularly from the base pipe.

8. The urea plant decomposer of claim 7, wherein the gas feed conduit is substantially T-shaped.

9. The urea plant decomposer of claim 1, wherein the base pipe includes at least two portions of at least one of: different cross sections to one another and eccentric with respect to one another.

10. The urea plant decomposer of claim 1, wherein the diffuser assembly defines at least one drain hole formed in one or more bottom end portions of the diffuser assembly to drain off any liquid penetrating the diffuser assembly.

11. The urea plant decomposer of claim 1, wherein the diffuser assembly includes at least one support which axially supports and angularly locks the diffuser assembly, said support including a bracket which defines a seat which receives a bottom end portion of the diffuser assembly resting axially on the bracket, inside the seat, the diffuser assembly having at least one fastener having two downward-facing lateral shoulders which cooperate with respective lateral edges of the seat.

12. The urea plant decomposer of claim 11, wherein the seat defines at least one drain hole formed through the bracket at the bottom of the seat to drain off any liquid collecting inside the seat.

13. The urea plant decomposer of claim 1, wherein the base pipe is perpendicular to the substantially cylindrical lateral wall and the axis.

14. The urea plant decomposer of claim 1, wherein the outlet is perpendicular to the axis.

15. The urea plant decomposer of claim 1, wherein said diffuser assembly is shaped to divert the passivating gas stream uniformly about the axis.

16. A urea plant decomposer with a gas diffusion system configured to feed a passivating gas stream into the urea plant decomposer extending along an axis, said urea plant decomposer comprising:
   a bottom holder which defines a chamber, said bottom holder including:
      a bottom portion of a casing, a bottom catch portion closed at a bottom end by a bottom wall, and having a substantially cylindrical lateral wall around the axis, and
      a funnel-shaped top diffusion portion which flares upwards, tapers towards the bottom catch portion and is bounded by a truncated-cone-shaped lateral wall around the axis;
   a gas feed conduit including:
      a base pipe transverse to the substantially cylindrical lateral wall and the axis, and a fitting which terminates with an opening defining an outlet which is transverse to the axis and from which the passivating gas stream flows substantially parallel to the axis, said outlet being located centrally inside the bottom holder and the defined chamber substantially about the axis, wherein said gas feed conduit projects inside the chamber from an inlet hole formed through the substantially cylindrical lateral wall of the bottom catch portion and said gas feed conduit terminates with said outlet; and a diffuser assembly including a central diffuser located over the outlet of the gas feed conduit, said central diffuser being aligned with the outlet along the axis and defining a plurality of radial gas outlet openings uniformly spaced about the axis, wherein the diffuser assembly is configured to diffuse the passivating gas stream from the gas feed conduit inside the chamber, said diffuser assembly being shaped to:

intercept the passivating gas stream flowing axially from the outlet, and divert the passivating gas stream substantially radially with respect to the axis and about the axis, wherein the central diffuser is associated with a distributor connected to the gas feed conduit to receive the passivating gas stream from the outlet of the gas feed conduit, said distributor being shaped to distribute at least part of the oncoming passivating gas stream radially to the central diffuser.

17. The urea plant decomposer of claim 16, wherein the central diffuser is positioned crosswise to the axis to obstruct the outlet from above and stop the passage of the passivating gas stream exiting from the outlet along the axis.

18. The urea plant decomposer of claim 16, wherein the central diffuser includes a dome-shaped hood having a peripheral edge spaced axially apart from the outlet and radially outwards with respect to the outlet.

19. The urea plant decomposer of claim 16, wherein the distributor is an axial distributor extending along or parallel to the axis, said axial distributor receives the passivating gas stream from the gas feed conduit along the axis.

20. The urea plant decomposer of claim 19, wherein the axial distributor includes a tubular member extending along the axis and defining a plurality of longitudinal slits formed through a lateral wall of the tubular member and parallel to one another and to the axis.

21. The urea plant decomposer of claim 20, wherein the slits are angularly spaced and uniformly distributed around the axis and elongated parallel to the axis.

22. The urea plant decomposer of claim 16, wherein the central diffuser surrounds the distributor along the axis.

23. The urea plant decomposer of claim 16, wherein the central diffuser includes a hollow body defining an inner seat bounded by a wall surrounding the distributor, said distributor being housed in the inner seat.

24. The urea plant decomposer of claim 23, wherein the central diffuser defines a plurality of radial gas outlet openings formed through the wall and defined by respective vertically elongated slots.

25. The urea plant decomposer of claim 24, wherein the central diffuser defines:

a first set of slots located on a top dome-shaped portion of the hollow body above a horizontal centreline plane of the hollow body and uniformly spaced about the axis, and a second set of slots located on a bottom dome-shaped portion of the hollow body below the horizontal centreline plane of the hollow body and uniformly spaced about the axis.

26. A urea plant decomposer with a gas diffusion system configured to feed a passivating gas stream into the urea plant decomposer extending along an axis, said urea plant decomposer comprising:

a bottom holder which defines a chamber, said bottom holder including:
a bottom portion of a casing,
a bottom catch portion closed at a bottom end by a bottom wall, and having a substantially cylindrical lateral wall around the axis, and
a funnel-shaped top diffusion portion which flares upwards, tapers towards the bottom catch portion and is bounded by a truncated-cone-shaped lateral wall around the axis;

a gas feed conduit including:
a base pipe transverse to the substantially cylindrical lateral wall and the axis, and
a fitting which terminates with an opening defining an outlet which is transverse to the axis and from which the passivating gas stream flows substantially parallel to the axis, said outlet being located centrally inside the bottom holder and the defined chamber substantially about the axis, wherein said gas feed conduit projects inside the chamber from an inlet hole formed through the substantially cylindrical lateral wall of the bottom catch portion and said gas feed conduit terminates with said outlet; and a diffuser assembly including a radial diffuser extending radially with respect to the axis, wherein the radial diffuser includes a plurality of arms uniformly spaced about the axis and which project radially from a distributor and which each define a plurality of downward-facing bottom gas outlet openings defined by respective slots spaced axially apart along said arm and located on a bottom portion of said arm, wherein said diffuser assembly is configured to diffuse the passivating gas stream from the gas feed conduit inside the chamber, said diffuser assembly being shaped to:

intercept the passivating gas stream flowing axially from the outlet, and
divert the passivating gas stream substantially radially with respect to the axis and about the axis.

27. The urea plant decomposer of claim 26, wherein the slots on each arm are elongated crosswise to the arm.

28. The urea plant decomposer of claim 26, wherein the radial diffuser is associated with a radial distributor extending along the axis and which receives the passivating gas stream from the outlet of the gas feed conduit and radially distributes the passivating gas stream to the radial diffuser.

29. The urea plant decomposer of claim 28, wherein the radial distributor is located at the outlet of the gas feed conduit and defines:

an axial inlet aligned along the axis and in communication with the outlet, and
a plurality of radial outlets angularly spaced apart from one another and uniformly distributed about the axis.

30. A urea plant decomposer with a gas diffusion system configured to feed a passivating gas stream into the urea plant decomposer extending along an axis, said urea plant decomposer comprising:

a bottom holder which defines a chamber, said bottom holder including:
a bottom portion of a casing,
a bottom catch portion closed at a bottom end by a bottom wall, and having a substantially cylindrical lateral wall around the axis, and a funnel-shaped top diffusion portion which flares upwards, tapers towards the bottom catch portion and is bounded by a truncated-cone-shaped lateral wall around the axis;

a gas feed conduit including:
   a base pipe transverse to the substantially cylindrical lateral wall and the axis, and
   a fitting which terminates with an opening defining an outlet which is transverse to the axis and from which the passivating gas stream flows substantially parallel to the axis, said outlet being located centrally inside the bottom holder and the defined chamber substantially about the axis, wherein said gas feed conduit projects inside the chamber from an inlet hole formed through the substantially cylindrical lateral wall of the bottom catch portion and said gas feed conduit terminates with said outlet; and a diffuser assembly including an annular central diffuser ring-shaped about the axis which defines a plurality of downward-facing bottom gas outlet openings uniformly distributed about the axis, wherein the annular central diffuser is connected to a radial distributor and the diffuser assembly is configured to diffuse the passivating gas stream from the gas feed conduit inside the chamber, said diffuser assembly being shaped to:
   intercept the passivating gas stream flowing axially from the outlet, and
   divert the passivating gas stream substantially radially with respect to the axis and about the axis.

31. The urea plant decomposer of claim 30, wherein the downward-facing bottom gas outlet openings are slots radially elongated with respect to the axis.

32. The urea plant decomposer of claim 30, wherein the annular central diffuser includes a hollow toroidal body which defines a plurality of inlets spaced angularly apart, facing the axis and connected to respective arms of a radial diffuser.

* * * * *